(12) United States Patent
Chan et al.

(10) Patent No.: US 10,836,738 B2
(45) Date of Patent: Nov. 17, 2020

(54) EPOXIDATION PROCESS WITH CONCENTRATED ETHYLENE OXIDE SOLUTIONS

(71) Applicant: Scientific Design Company, Inc., Little Ferry, NJ (US)

(72) Inventors: Chun Chau Chan, Brooklyn, NY (US); Eunice Yamada, Pittstown, NJ (US); Barry Jay Billig, Irvington, NY (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 16/399,045

(22) Filed: Apr. 30, 2019

(65) Prior Publication Data

US 2019/0330170 A1 Oct. 31, 2019

Related U.S. Application Data

(60) Provisional application No. 62/664,474, filed on Apr. 30, 2018.

(51) Int. Cl.
| | | |
|---|---|---|
| *C07D 301/08* | (2006.01) | |
| *B01D 53/14* | (2006.01) | |
| *B01D 53/18* | (2006.01) | |
| *B01D 3/34* | (2006.01) | |
| *C07D 301/32* | (2006.01) | |
| *B01D 3/06* | (2006.01) | |
| *B01J 37/02* | (2006.01) | |
| *B01J 23/50* | (2006.01) | |

(52) U.S. Cl.
CPC ............. *C07D 301/08* (2013.01); *B01D 3/06* (2013.01); *B01D 3/346* (2013.01); *B01D 53/1431* (2013.01); *B01D 53/1487* (2013.01); *B01D 53/18* (2013.01); *C07D 301/32* (2013.01); *B01J 23/50* (2013.01); *B01J 37/0201* (2013.01)

(58) Field of Classification Search
CPC ................................ C07D 301/08; B01D 3/06
USPC ................................................... 549/541, 532
See application file for complete search history.

(56) References Cited

U.S. PATENT DOCUMENTS

| | | |
|---|---|---|
| 3,028,434 A | 4/1962 | Weisz et al. |
| 3,563,914 A | 2/1971 | Wattimena |
| 3,702,259 A | 11/1972 | Nielsen |
| 3,867,113 A | 2/1975 | Foster et al. |
| 3,957,698 A | 5/1976 | Hatch |
| 4,160,116 A | 7/1979 | Mieno et al. |

(Continued)

FOREIGN PATENT DOCUMENTS

| | | |
|---|---|---|
| CN | 1208135 A | 2/1999 |
| CN | 103709001 A | 4/2014 |

(Continued)

OTHER PUBLICATIONS

International Search Report dated Aug. 12, 2019, received in International Application No. PCT/US2019/029830.

(Continued)

*Primary Examiner* — Daniel R Carcanague
(74) *Attorney, Agent, or Firm* — Scully Scott Murphy and Presser

(57) ABSTRACT

An improved process for the recovery of ethylene oxide from the aqueous scrubbing solution in which the ethylene oxide is recovered into a vaporous stream highly enriched in ethylene oxide.

9 Claims, 1 Drawing Sheet

(56) References Cited

U.S. PATENT DOCUMENTS

| | | |
|---|---|---|
| 4,165,440 A | 8/1979 | Kim |
| 4,519,875 A | 5/1985 | Becker et al. |
| 4,761,394 A | 8/1988 | Lauritzen |
| 4,766,105 A | 8/1988 | Lauritzen |
| 4,778,567 A | 10/1988 | Kakimoto et al. |
| 4,875,909 A | 10/1989 | Kakimoto et al. |
| 4,908,343 A | 3/1990 | Bhasin |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |
| 5,187,140 A | 2/1993 | Thorsteinson et al. |
| 5,407,888 A | 4/1995 | Herzog et al. |
| 5,763,691 A | 6/1998 | Kawabe et al. |
| 5,945,568 A | 8/1999 | Nagata et al. |
| 6,160,187 A | 12/2000 | Strickler et al. |
| 6,211,419 B1 | 4/2001 | Strickler et al. |
| 7,453,015 B2 | 11/2008 | Van Kruchten et al. |
| 7,663,005 B2 | 2/2010 | Crudge et al. |
| 7,683,221 B2 | 3/2010 | Powell et al. |
| 8,183,400 B2 * | 5/2012 | Szul .................... C07D 301/32 202/197 |
| 2002/0082456 A1 | 6/2002 | Van Kruchten et al. |
| 2005/0119510 A1 | 6/2005 | Boons et al. |
| 2006/0161026 A1 | 7/2006 | Van Kruchten |
| 2006/0183927 A1 | 8/2006 | Billig et al. |
| 2007/0037991 A1 | 2/2007 | Rizkalla |
| 2017/0298035 A1 | 10/2017 | Olthof |

FOREIGN PATENT DOCUMENTS

| | | | |
|---|---|---|---|
| CN | 104974115 A * | 10/2015 | ........... C07D 303/04 |
| EP | 0123700 A1 | 11/1984 | |
| EP | 0123709 A1 | 11/1984 | |
| EP | 1828086 B1 | 10/2009 | |
| EP | 2121646 B1 | 2/2011 | |
| JP | 2010528113 A | 8/2010 | |
| WO | 0035840 A1 | 6/2000 | |
| WO | 2006072766 A1 | 7/2006 | |
| WO | 2008150338 A1 | 12/2008 | |
| WO | 2009105252 A1 | 8/2009 | |
| WO | 2017178418 A1 | 10/2017 | |

OTHER PUBLICATIONS

International Search Report dated Aug. 13, 2019, received in International Application No. PCT/US2019/029820.

International Search Report dated Aug. 13, 2019, received in International Application No. PCT/US2019/029818.

International Search Report dated Aug. 16, 2019, received in International Application No. PCT/US2019/029825.

Shvets, V. F., et al., "The Model of Catalytic Reactor of Ethylene Glycol Production", Organic Process Research & Development, Published on web Nov. 2, 2005, pp. 768-773, vol. 9, No. 6.

Office Action dated Nov. 25, 2019 received in U.S. Appl. No. 16/398,975.

* cited by examiner

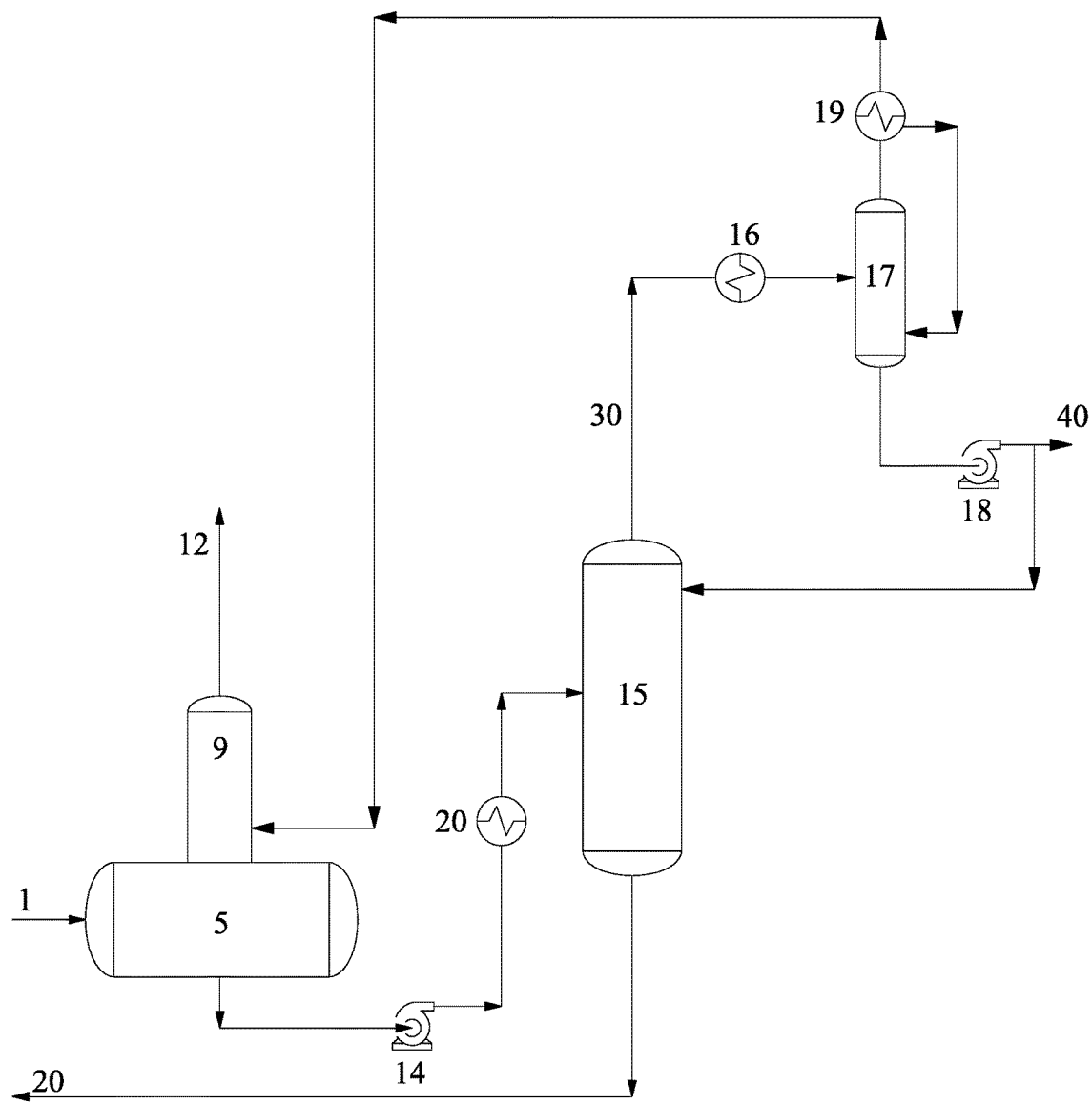

EPOXIDATION PROCESS WITH CONCENTRATED ETHYLENE OXIDE SOLUTIONS

CROSS REFERENCE TO RELATED APPLICATION

The present invention claims the benefit of U.S. Provisional Patent Application No. 62/664,474 filed Apr. 30, 2018, the entire content and disclosure of which is incorporated herein by reference.

FIELD OF THE INVENTION

The present invention relates to a method for the oxidation of ethylene into ethylene oxide.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Theodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 25 billion tons. One of the reasons that ethylene oxide is such a widely produced chemical product is its startling versatility—it is the starting point for innumerable derivatives including ethylene glycol ethoxylates, ethanolamines, polyols, and glycol ethers each of which becomes the raw material for numerous high-value products such as fabrics, moldable plastics, surfactants, detergents, solvents and many other.

Most conventional ethylene oxide processes, however, do not allow their operators to take full advantage of this versatility. In conventional ethylene oxide processes, ethylene oxide along with inerts, unreacted and byproduct gases are present in the liquid bottoms from the scrubbing column and the liquid bottoms stream thus taken from the scrubbing column is subjected to extensive further processing to separate the ethylene oxide from these other components. At the end of these process steps most typically the unreacted and inert gases are recycled to the ethylene oxide reactor, byproducts and other gas components vented to the atmosphere (if allowed by local admissions regulations), and the ethylene oxide is present in a highly diluted aqueous solution (typically comprising about 10% to 15% ethylene oxide) that can be processed further into ethylene glycol and which has been rendered considerably inert against possible further reactions or events and thus suitable for long-term storage or even shipment.

While this conventional system has many advantages, and hence why it has formed the backbone of the ethylene oxide process that is the most widely-licensed in the world, it has the disadvantage of being both energy intensive and less versatile than desired. While this highly dilute solution of ethylene oxide is ideal for making ethylene glycol (because the hydrolysis reaction is typically carried out at high ratios of water to ethylene oxide to reduce higher glycol production), before it can be used downstream in producing ethylene oxide derivatives it must be concentrated in successive evaporator trains that are not only high capital cost items but also require considerable amount of energy to operate.

The conventional process has been designed and optimized primarily for producing ethylene glycol and given that in excess of 70% of yearly ethylene oxide production is converted into ethylene glycol, it is understandable why this process configuration has formed the backbone of the ethylene oxide process that is the most widely-licensed in the world. But while this highly dilute solution of ethylene oxide is ideal for making ethylene glycol (because the hydrolysis reaction is typically carried out at high ratios of water to ethylene oxide to reduce higher glycol production), before it can be used downstream in producing ethylene oxide derivatives it must be concentrated in successive evaporator trains that are not only high capital cost items but also require considerable amount of energy to operate.

Accordingly, there is a need in the art for recovering ethylene oxide from the aqueous scrubbing solution in a more concentrated solution that can then be converted to one of the many highly desirable ethylene oxide derivatives without the aforementioned requirement of concentrating the solution.

BRIEF SUMMARY OF THE INVENTION

The present invention relates to a process for the preparation of an enriched ethylene oxide stream comprising the steps of: providing a rich cycle water stream containing ethylene oxide, methane, and ethylene; separating, in a flash drum, a light gas solute vapor from the rich cycle water stream; directing upwardly the light gas solute vapor through an opening in the flash drum allowing fluid communication to an absorber affixed to the top surface of the flash drum to form the absorber overhead; pumping the rich cycle water from a liquid bottoms of the flash drum to a stripper; and separating, in the stripper, the rich cycle water into: (1) an enriched overhead stripper stream comprising at least about 40 mol %, preferably at least about 50 mol % ethylene oxide; and (2) a lean cycle water solution in the stripper bottoms containing about 1 to about 50 molar ppm ethylene oxide in the stripper bottoms.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 is a schematic flow sheet for a process for preparing a concentrated ethylene oxide stream according to the present invention.

DETAILED DESCRIPTION OF THE INVENTION

All parts, percentages and ratios used herein are expressed by volume unless otherwise specified. All documents cited herein are incorporated by reference.

By "water" it is meant any kind of water suitable for use in chemical and petrochemical processing, including deionized, demineralized, industrial, potable and distilled water.

An improved process has been discovered in the present invention for the recovery of ethylene oxide from the aqueous scrubbing solution in which the ethylene oxide is recovered into a vaporous stream highly enriched in ethylene oxide. Because the stream has a high content of ethylene oxide it is highly versatile for use further downstream in producing ethylene oxide derivatives while the high temperature and pressure of the stream (outside of ethylene oxide, the balance of which is steam) make it useful to improve heat integration and reduce utility costs downstream.

The use of this invention will now be described below in greater detail, below, as a component of an ethylene oxide production process.

Ethylene oxide is produced by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 30% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more reaction moderators, non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

As mentioned above, a usual method for the ethylene epoxidation process comprises the vapor-phase oxidation of ethylene with molecular oxygen, in the presence of an epoxidation catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long, each filled and packed with catalyst. The reaction feed mixture (described above) is introduced into these tubes, and the resulting reactor effluent gas contains ethylene oxide, un-used reactants, and byproducts.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The reactor effluent exits through the reactor outlet, is cooled and flows to the EO scrubbing column, where the reactor effluent is contacted with recirculated lean cycle water to absorb the ethylene oxide as well as several "light" solutes contained the reactor effluent.

In FIG. 1 the scrubbing column liquids (hereinafter referred to as the "rich cycle water" stream) flows through conduit 1 and is supplied to a flash drum 5. The rich cycle water stream is an aqueous stream comprising 1.5 mol % to 4 mol % ethylene oxide as well as other inert and unreacted gases supplied as components of the reactor feed such as methane, ethylene and oxygen. Byproducts such as carbon dioxide may also be present as well as with ppm levels of impurities. This rich cycle water stream is supplied at a pressure of preferably between about 0.5 atm to about 6 atm to the flash drum 5. An absorber unit 9 is permanently and directly affixed to the top surface of the flash drum 5 and an opening is provided in the flash drum for communication with the absorber 9. In the present invention the pressure in both the flash drum 5 and absorber 9 assembly is maintained within a sufficient range so that when the rich cycle water enters the flash drum 5 the "light" gases that are solutes in the rich cycle water that have a volatility greater than that of ethylene oxide flash out of rich cycle water on entering the flash drum 5 and the light gas vapor is directed by pressure differential between the flash drum 5 and the absorber 9 to rise upwardly through the opening into the absorber 9 to form the overhead of the absorber 9, while the ethylene oxide solute stays largely solubilized within the rich cycle water stream in the liquid bottoms of the flash drum 5. These more volatile "light" gases include the aforementioned inert, unreacted or byproduct gas rich cycle water solutes (in addition, traces of ethylene oxide may also vaporize with the more volatile light gases in the rich cycle water stream.) The small amounts of ethylene oxide that effervesce out of the rich cycle water, and rise into the absorber 9 with the light gas solute vapor may be recovered by an downwardly-moving wash stream (not shown) to absorb and recover the upwardly moving ethylene oxide.

As mentioned above, the absorber 9 is directly and permanently affixed to the top surface of the flash drum 5, by for example, welding. The absorber 9 is affixed to the flash drum 5 in the same manner as a still-column and reboiler configuration well-known to those skilled in the art. More specifically, the absorber 9 is affixed to the flash drum 5 along the longitudinal axis of the flash drum 5 but is preferably fixed at the midpoint of the longitudinal axis. The cross-section of the absorber 9 matches the shape of the opening in the flash drum 5 over which the absorber 9 is affixed and which allows communication between the flash drum 5 and the absorber 9. The cross-section of the absorber and the shape of the opening in the flash drum 5 have the same matching shape and that shape may be any shape between a circle and an ellipse, between an eccentricity of 0 and an eccentricity of 1. The opening in the flash drum 5 and the absorber 9 are aligned so that the center of the opening is collinear with the center of the absorber 9. Configuring the opening in the flash drum 5 and the shape of the absorber 9 and their respective alignments ensures that there is proper fluid communication between these two elements. The absorber 9 is preferably welded flush to the inner diameter of the opening made in the flash drum 5 so that the outer diameter of the absorber 9 is flush with the diameter of the opening in the flash drum 5. Alternatively, the opening in the flash drum 5 may have a diameter equal to the inside diameter of the absorber 9.

In order to ensure the balance between flashing the more volatile "light" solutes while maintaining high solubility of ethylene oxide in the rich cycle water, the pressure in the flash drum 5 is maintained at about 1 atm to about 3 atm and the pressure in the absorber 9 to which there is direct communication is just slightly lower than the pressure in the flash drum 5. The temperature of the gases at the top of the absorber 9 is from about 30° C. to about 45° C., while the temperature in the flash drum 5 is from about 50° C. to about 60° C.

The overhead components in conduit 12 of the absorber 9 are compressed and returned to the upstream reaction section (not shown) as possible recycle to the reactor. The rich cycle water flows as liquid bottoms from the flash drum 5 through pump 14 and through optional heat exchanger 20 (which preheats the stream) and to the stripper 15. The temperature in the stripper 15 overhead to be from about 25° C. to about 100° C. and the stripper 15 bottoms is about 100° C. to about 200° C. The rich cycle water stream can be pre-heated in heat exchanger 20 to reduce the duty necessary to operate the stripper 15. The pressure in the stripper 15 is maintained within a range of about 2 atm to about 6 atm. The separation efficiency of EO from the rich cycle water may also be enhanced by use of a steam ejector system well-known to those skilled in the art, with steam supplied from either: (1) steam generated elsewhere in the ethylene oxide production facility or (2) medium- or high-pressure steam supplied externally/OSBL; or a combination of these two sources.

The pressurized overhead stripper stream flows through conduit 30 for further processing into ethylene oxide derivatives. Compared to the highly diluted aqueous solution found at a comparable location in the separation section of the conventional process, the enriched vaporous stripper overhead stream is considerably more enriched in ethylene oxide, containing preferably at least about 40 mol %, preferably at least about 50 mol % ethylene oxide with the balance of the overhead stripper stream being vapor-steam. The overhead stripper stream is thus supplied both at high concentrations of ethylene oxide (although always below the deflagration and detonation limit) and at high pressure. This makes the stream extremely useful for further processing into ethylene oxide derivatives on a highly economical basis as the stream does not to be enriched nor pressurized nor vaporized in a downstream processing step for ethylene oxide derivatives. In fact, the relatively high temperature and higher pressure stripper overhead stream presents many heat integration opportunities and may be useful in reducing utility cost and burden further downstream in a derivatives unit.

Another advantageous process option of the present invention is that the liquid bottoms of the stripper 15, which is a lean cycle water solution containing little ethylene oxide (from about 1 molar ppm to about 50 molar ppm) and which is also free of light components as well as impurities, may in preferable embodiments be used in a variety of other heat integration schemes elsewhere in the plant depending on need and conditions.

Under these circumstances of streams having a higher than typical ethylene oxide concentration, operators will continue to maintain appropriate safety standards that are always observed when producing, handling or storing ethylene oxide. As always, measures must be taken to prevent reactions or events that could result in ignition, combustion, deflagration, detonation or explosion of any gas stream, but especially those containing higher than typical concentrations of ethylene oxide. Accordingly, to prevent such events relief valves may be used to relieve or reduce undesirable pressure built-up in the process, reaction, or separation systems or elsewhere in the ethylene oxide plan both upstream and downstream of what is illustrated. The separation in the stripper 15 is so effective that nearly all of the ethylene oxide in the rich cycle water that enters the stripper 15 is successfully separated and recovered from the rich cycle water and leaves the stripper 15 as vapor overhead while only a small portion leaves the stripper 15 as liquid bottoms.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.) Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. In one embodiment, the catalytic effective amount of silver is from 10% by weight to 45% by weight. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766, 105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

For purposes of illustration only, the following are conditions that are often used in current commercial ethylene oxide reactor units: a gas hourly space velocity (GHSV) of 1500-10,000 h$^{-1}$, a reactor inlet pressure of 1 MPa to 3 MPa, a coolant temperature of 180-315° C., an oxygen conversion level of 10-60%, and an EO production rate (work rate) of 100-350 kg EO/m$^3$ catalyst/hr and a change in ethylene oxide concentration, ΔEO, of from about 1.5% to about 4.5%. The feed composition in the reactor inlet after the completion of start-up and during normal operation typically comprises (by volume %) 1-40% ethylene, 3-12% O$_2$; 0.2% to 10%, preferably 0.2% to 6%, more preferably 0.2% to 5% of CO$_2$; 0-5% ethane, an amount of one or more chloride moderators, which are described herein; and the balance of the feed being comprised of argon, methane, nitrogen or mixtures thereof.

We claim:

1. A process for the preparation of an enriched ethylene oxide stream comprising the steps of:
   (a) providing a rich cycle water stream containing ethylene oxide, methane, and ethylene;
   (b) separating, in a flash drum, a light gas solute vapor from the rich cycle water stream;
   (c) directing upwardly the light gas solute vapor through an opening in the flash drum allowing fluid communication to an absorber affixed to a top surface of the flash drum to form an absorber overhead, wherein the opening in the flash drum and the absorber are aligned such that the opening of the flash drum is collinear with a center of the absorber;
   (d) pumping the rich cycle water from a liquid bottoms of the flash drum to a stripper; and
   (e) separating, in the stripper, the rich cycle water stream into: (1) an enriched vaporous overhead stripper stream comprising at least about 40 mol % ethylene oxide; and (2) a lean cycle water solution in the stripper bottoms containing about 1 to about 50 molar ppm ethylene oxide in the stripper bottoms, wherein the stripper bottoms has a temperature from about 100° C. to about 200° C., the enriched vaporous overhead stripper stream has a temperature from about 25° C. to about 100°, and the enriched vaporous overhead stripper stream is a pressured stream having a pressure from about 2 from atmospheres to about 6 atmospheres.

2. The process according to claim 1 wherein the light gas solute vapor contains methane, ethylene, and oxygen.

3. The process according to claim 1 wherein the pressure in the flash drum is between 1 atm and 3 atm.

4. The process according to claim 1 wherein the rich cycle water in the liquid bottoms of the flash drum contain from about 1.5 mol % to about 4 mol % ethylene oxide.

5. The process according to claim 1 wherein the rich cycle water is preheated between the flash drum and the stripper.

6. The process according to claim 1 wherein the cross-section of the absorber matches the shape of the opening in the flash drum.

7. The process according to claim 1 wherein the absorber further comprises a downwardly-moving wash stream for absorbing vaporous ethylene oxide.

8. The process of claim 1 wherein the enriched vaporous overhead stripper stream comprises at least about 50 mol % ethylene oxide.

9. The process of claim 1 wherein the enriched vaporous overhead striper stream containing at least 40 mole % ethylene oxide is obtained directly in the stripper and without any evaporator trains.

* * * * *